(12) United States Patent
Meral et al.

(10) Patent No.: US 11,660,069 B2
(45) Date of Patent: May 30, 2023

(54) COMBINING IMAGE BASED AND INERTIAL PROBE TRACKING

(71) Applicant: KONINKLIJKE PHILIPS N.V., Eindhoven (NL)

(72) Inventors: Faik Can Meral, Mansfield, MA (US); Jochen Kruecker, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 211 days.

(21) Appl. No.: 16/955,204

(22) PCT Filed: Dec. 11, 2018

(86) PCT No.: PCT/EP2018/084255
§ 371 (c)(1),
(2) Date: Jun. 18, 2020

(87) PCT Pub. No.: WO2019/121127
PCT Pub. Date: Jun. 27, 2019

(65) Prior Publication Data
US 2020/0337673 A1 Oct. 29, 2020

Related U.S. Application Data

(60) Provisional application No. 62/607,395, filed on Dec. 19, 2017.

(51) Int. Cl.
*A61B 8/00* (2006.01)
*A61B 8/08* (2006.01)

(52) U.S. Cl.
CPC .......... *A61B 8/4245* (2013.01); *A61B 8/4254* (2013.01); *A61B 8/4263* (2013.01); *A61B 8/463* (2013.01); *A61B 8/5246* (2013.01)

(58) Field of Classification Search
CPC ... A61B 8/4245; A61B 8/4254; A61B 8/4263; A61B 8/463; A61B 8/5246
See application file for complete search history.

(56) References Cited

U.S. PATENT DOCUMENTS 3,727,165 A 4/1973 Hagen
6,122,538 A 9/2000 Sliwa, Jr.
(Continued)

FOREIGN PATENT DOCUMENTS

AU 2011100208 3/2011
JP 2017006370 A 1/2017
(Continued)

OTHER PUBLICATIONS

PCT International Search Report, International application No. PCT/EP2018/084255, dated Mar. 26, 2019.
(Continued)

*Primary Examiner* — Joel Lamprecht
*Assistant Examiner* — Brooke Lyn Klein
(74) *Attorney, Agent, or Firm* — Sherry Austin

(57) ABSTRACT

An ultrasound imaging system with an inertial tracking sensor (20) rigidly fixed to an ultrasound probe (10). In a first embodiment, a real-time pose estimation unit (32) enhances image based tracking using the inertial data stream to calculate out-of-plane angles of rotation and determine an out-of-plane translation by iteratively selecting planes with the estimated out-of-plane rotations with varying out-of-plane offset, computing the differences between sub-plane distances computed by speckle analysis and the selected plane minimizing for the root mean square of the differences for all selected planes. In another embodiment, the real-time pose estimation unit enhances inertial tracking using the ultrasound image data stream to estimate an in-plane rota- (Continued)

tion angle; and substituting the in-plane rotation angle for an angle of rotation estimated using the inertial data stream.

6 Claims, 9 Drawing Sheets

(56) References Cited

U.S. PATENT DOCUMENTS

| | | | |
|---|---|---|---|
| 6,315,724 B1 | 11/2001 | Berman | |
| 10,290,098 B2 | 5/2019 | Bharat | |
| 2008/0146942 A1 | 6/2008 | Dala-Krishna | |
| 2010/0022871 A1 | 1/2010 | De Beni | |
| 2012/0277588 A1* | 11/2012 | Padfield | A61B 8/4263 |
| | | | 600/443 |
| 2013/0320143 A1 | 12/2013 | Chaumel et al. | |
| 2014/0128739 A1 | 5/2014 | Sundaran | |
| 2016/0314715 A1* | 10/2016 | Savitsky | G09B 23/286 |
| 2016/0328998 A1* | 11/2016 | Pedersen | A61B 8/4245 |
| 2017/0273665 A1* | 9/2017 | Kapoor | A61B 6/12 |
| 2019/0029756 A1 | 1/2019 | Natarajan | |
| 2019/0142374 A1 | 5/2019 | Kruecker | |

FOREIGN PATENT DOCUMENTS

| | | |
|---|---|---|
| WO | 2006127142 A2 | 11/2006 |
| WO | 2009149499 A1 | 11/2009 |
| WO | 2017102761 A1 | 6/2017 |

OTHER PUBLICATIONS

Housden, R. J., et al., "Sensorless Reconstruction of Unconstrained Freehand 3D Ultrasound Data", Ultrasound in Medicine & Biology, vol. 33, No. 3, pp. 408-419, 2007.

* cited by examiner

COMBINING IMAGE BASED AND INERTIAL PROBE TRACKING

CROSS-REFERENCE TO RELATED APPLICATIONS

This patent application claims the priority benefit under 35 U.S.C. § 371 of International Patent Application no. PCT/EP2018/084255 filed Dec. 11, 2018, which claims the benefit of U.S. Application Serial No. 62/607,395, filed on Dec. 19, 2017. These applications are hereby incorporated by reference herein in their entirety.

FIELD OF THE INVENTION

The invention relates to the field of ultrasound probe tracking and more particularly to ultrasound probe tracking using integrated ultrasound image-based and inertial tracking data.

BACKGROUND

In medical procedures, real-time information about the spatial position and orientation (i.e. the "pose") of a medical device is often required. Typically, such information is obtained using optical, electro-magnetic, or ultrasound tracking systems. Such systems are expensive and sometimes require significant setup time and effort. For some procedures, the device to be tracked is an imaging device (e.g. an ultrasound probe), the requirements for accuracy of the device position tracking are less stringent, and any errors can be easily recognized and corrected interactively by the operator. One example for such a procedure is ultrasound-guided prostate biopsy, in particular, ultrasound-MRI fusion biopsy using the Philips Invivo UroNav® system. For such procedures, it is desirable to use lower-cost spatial tracking systems and methods that are easily set up and fulfil the moderate accuracy requirements of the procedure.

Ultrasound image based tracking methods are known in the art. A description of ultrasound based tracking can be found in Housden, R. J. et al. "Sensorless reconstruction of unconstrained freehand 3D ultrasound data", Ultrasound in Medicine and Biology 33(3), 408-419 (2007).

Ultrasound image based tracking methods can be used to estimate the in-plane motion in the imaging plane (translation in image x and image y and rotation around the axis normal to the imaging plane), as well as motion out of the imaging plane. In-plane estimation is identical to the problem of image registration. Out of plane motion estimations use the more complicated speckle decorrelation method. In this method, the out of plane distances between two images can be estimated based on calibrations from previously obtained image sets with known frame spacing.

Micro electro-mechanical (MEMS) inertial tracking sensors (three axis accelerometer and three-axis gyroscope assemblies) or inertial measurement units (IMU), have emerged in recent years that can be mass-produced at extremely low cost that have reached accuracy levels on the order of milli-g (i.e. 10 mm/s$^2$) for linear acceleration, and a few degrees per hour bias stability for rotation.

Using gyroscope and accelerometer sensors (inertial measurement unit or "IMU" sensors, or MEMS) for ultrasound probe tracking and volumetric reconstruction of ultrasound images is appealing. Bias and noise associated with these inertial sensors, however, limit their accuracy. Sensor fusion methods using IMU sensors and gravitational acceleration as reference demonstrate significant improvement for pose estimation. These methods, however, are underdetermined due to the lack of a reliable secondary reference, such as the Earth's magnetic field, which is not an ideal candidate to be used as a reference indoors or in clinical environments due to large distortions.

The combination of ultrasound image based tracking with inertial sensors (IMU, gyroscope, MEMS) attached to the ultrasound probe can be used for "low-cost tracking", i.e. for spatial localization of the probe position at much lower cost than conventional tracking methods such as electromagnetic (EM) tracking.

SUMMARY

Image based tracking, especially in the out-of-plane direction, gets complex for freehand scans, where the probe motion can comprise six degrees of freedom (DOF's), i.e. three translations and three rotations. These complicated scan geometries result in inaccurate and unreliable tracking performance. One of the most challenging problems with image based tracking is related to the directionality of decorrelation based distance estimates (i.e. out-of-plane motion toward the "front" or "back" of the current image plane) which is undetermined. An especially complicated case of the out-of-plane directionality problem occurs when two image planes intersect with the axis of rotation of the final image plane relative to the initial image plane going through the initial image plane.

According to a first aspect of a first embodiment of the present invention, an ultrasound imaging system is provided with enhanced ultrasound imaging probe tracking. The ultrasound imaging system comprises: an ultrasound imaging probe providing an image data stream of sequential image frames; an inertial tracking unit rigidly fixed to the ultrasound probe and providing an inertial data stream; and a real-time pose estimation unit receiving and processing the image data stream and the inertial data stream to estimate the ultrasound probe pose for a successive image frame. To estimate the ultrasound probe pose, the pose estimation unit: computes in-plane registration between an initial image frame and a successive image frame to determine in-plane translations and in-plane rotation from imaging data; divides the initial image frame and the registered successive image frame into a matrix of sub-planes; estimates out of plane absolute distances for each sub-plane using speckle decorrelation analysis; estimates out of plane rotation from the inertial data; iteratively selecting planes with the estimated out-of-plane rotations by varying an out-of-plane offset, calculating the motion of each sub-plane for the estimated out-of-plane rotations and the selected plane, computing the differences between the sub-plane absolute distances computed by speckle analysis and those calculated from the inertial data derived rotation and selected plane, and minimizing for the root mean square of the differences for all selected planes.

In one preferred embodiment the inertial tracking unit is an inertial measurement unit (IMU) comprising three mutually perpendicular angular acceleration sensors and three mutually perpendicular gyroscope sensors and the inertial data stream comprises angular acceleration data from the acceleration sensors and orientation data from the gyroscope sensors.

In one preferred embodiment the pose estimation unit is realized in a workstation. The workstation may further comprise an application unit applying the estimated ultrasound probe poses to fuse the image data for each pose with an image volume to generate a fused image and display the fused image on a display.

According to another aspect, a method for tracking an ultrasound imaging probe is provided. The method comprises the steps of: receiving an image data stream comprising successive image frames from the ultrasound probe and an inertial data stream from an inertial sensor unit rigidly attached to the ultrasound imaging probe; computing in-plane registration between an initial image frame and a successive image frame to determine in-plane translations and in-plane rotation from imaging data; dividing the initial image frame and the registered successive image frame into a matrix of sub-planes; estimating out of plane absolute distances for each sub-plane using speckle decorrelation analysis; estimating out of plane rotation from the inertial data; iteratively selecting planes with the estimated out-of-plane rotations by varying an out-of-plane offset, calculating the motion of each sub-plane for the estimated out-of-plane rotations and the selected plane, computing the differences between the sub-plane absolute distances computed by speckle analysis and those calculated from the inertial data derived rotation and selected plane, and minimizing for the root mean square of the differences for all selected planes.

In one preferred embodiment the method further comprises the steps of: assigning the plane with the minimum root mean square of differences as the final pose estimate; and applying the final pose to fuse successive images for display during an imaging procedure.

Inertial sensor fusion algorithms use gravity and earth's magnetic field as references to account for the drift in gyroscope angles. Earth's magnetic field, however, is not a reliable reference for indoor applications or clinical settings. These algorithms were designed for global navigation and aviation applications. In indoor clinical settings, nearby metal objects and electronic devices with their own electromagnetic fields distort the earth's magnetic field such that it is not reliable to use as a reference. Gravity still provides a useful reference for the pitch and roll rotations of the imaging object. Lacking a reference in the horizontal plane, gravity alone is not sufficient to obtain the exact pose of an imaging probe. Accumulating sensor bias can then cause significant drift around the vertical axis over extended periods of data acquisition. If inertial sensors are attached to an imaging device, such as an ultrasound imaging probe, then robust information from image based tracking, particularly, rotation in the imaging plane, can be substituted for the corresponding inertial (gyroscope) data before sensor fusion. This results in more accurate estimations after fusion.

According to another embodiment of the present invention, another ultrasound imaging system with enhanced ultrasound imaging probe tracking is provided. This ultrasound imaging system comprises: an ultrasound imaging probe providing an image data stream of sequential image planes; an inertial tracking unit rigidly fixed to the ultrasound probe and providing an inertial data stream, the inertial tracking unit measuring angular acceleration and tilt for three mutually perpendicular axes; a real-time pose estimation unit receiving and processing the image data stream and the inertial data stream to estimate a ultrasound probe pose. The pose estimation unit estimates an ultrasound probe pose by: using the ultrasound image data stream to estimate an in-plane rotation angle; and performing inertial tracking using the inertial tracking data stream, substituting the in-plane rotation angle estimated from the ultrasound image data stream for an angle of rotation estimated using the inertial data stream.

According to one preferred embodiment, the inertial tracking unit is an inertial measurement unit (IMU) comprising three mutually perpendicular angular acceleration sensors and three mutually perpendicular gyroscope sensors and the inertial data stream comprises angular acceleration data from the acceleration sensors and orientation data from the gyroscope sensors.

In one preferred embodiment the pose estimation unit is realized in a workstation.

The workstation may further comprise an application unit applying the estimated ultrasound probe poses to fuse the image data for each pose with an image volume to generate a fused image and display the fused image on a display.

According to another aspect, a method for tracking an ultrasound imaging probe is provided. The method comprises the steps of: receiving an image data stream comprising successive image planes from the ultrasound probe and an inertial data stream from an inertial sensor unit; using the ultrasound image data stream to estimate an in-plane rotation angle; and performing inertial tracking using the inertial tracking data stream, substituting the in-plane rotation angle estimated from the ultrasound image data stream for an angle of rotation estimated using the inertial data stream.

According to one preferred embodiment the angle of rotation estimates from the ultrasound imaging data are up-sampled to match the inertial sensor data sampling rate by interpolation.

BRIEF DESCRIPTION OF THE DRAWINGS

The features and advantages of the invention will be more clearly understood from the following detailed description of the preferred embodiments when read in connection with the accompanying drawing. Included in the drawing are the following figures.

DETAILED DESCRIPTION

Figure 1:
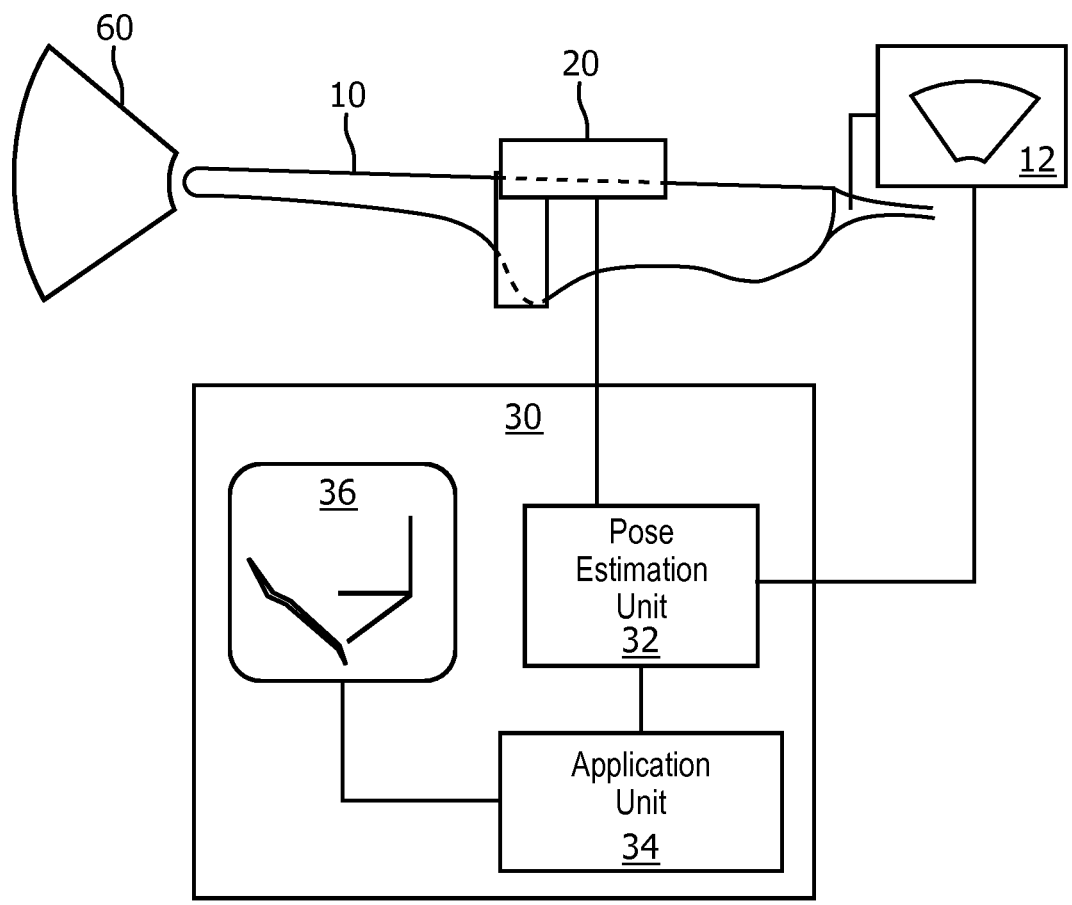
FIG. 1 is a block diagram of an ultrasound imaging system according to an embodiment of the present invention.

FIG. 1 shows an ultrasound imaging system with enhanced ultrasound imaging probe tracking according to an embodiment of the present invention. A hand held ultrasound imaging probe 10 comprises an ultrasound scanner 12 which is a transducer that performs a 2D scan of an ultrasound image plane 60, as is known in the art. Motion is applied to the ultrasound imaging probe 10 to generate a sequence of successive ultrasound image planes. These successive image planes or "frames" are transmitted by the ultrasound imaging probe as an imaging data stream 2.

An inertial tracking sensor 20 is rigidly fixed to the ultrasound imaging probe 10. The inertial tracking sensor may be fixed using any suitable fixing technique (e.g., bonding, mechanical fasteners, straps, integrally embedded in the probe, etc.). Preferably, the inertial tracking sensor may be an inertial measurement unit (IMU) or a micro electro-mechanical system (MEMS) navigation sensor which can measure both linear acceleration and tilt/rotation. An inertial sensor data stream 1 comprising angles of rotation about mutually perpendicular axes is transmitted by the inertial sensor 20.

In one preferred embodiment, the inertial tracking sensor 20 is fixed such that the sensor axes are aligned with the image axes of the ultrasound imaging probe. Alternatively, the axes of the inertial tracking sensor 20 can be calibrated to the image axes prior to tracking.

Figure 2:
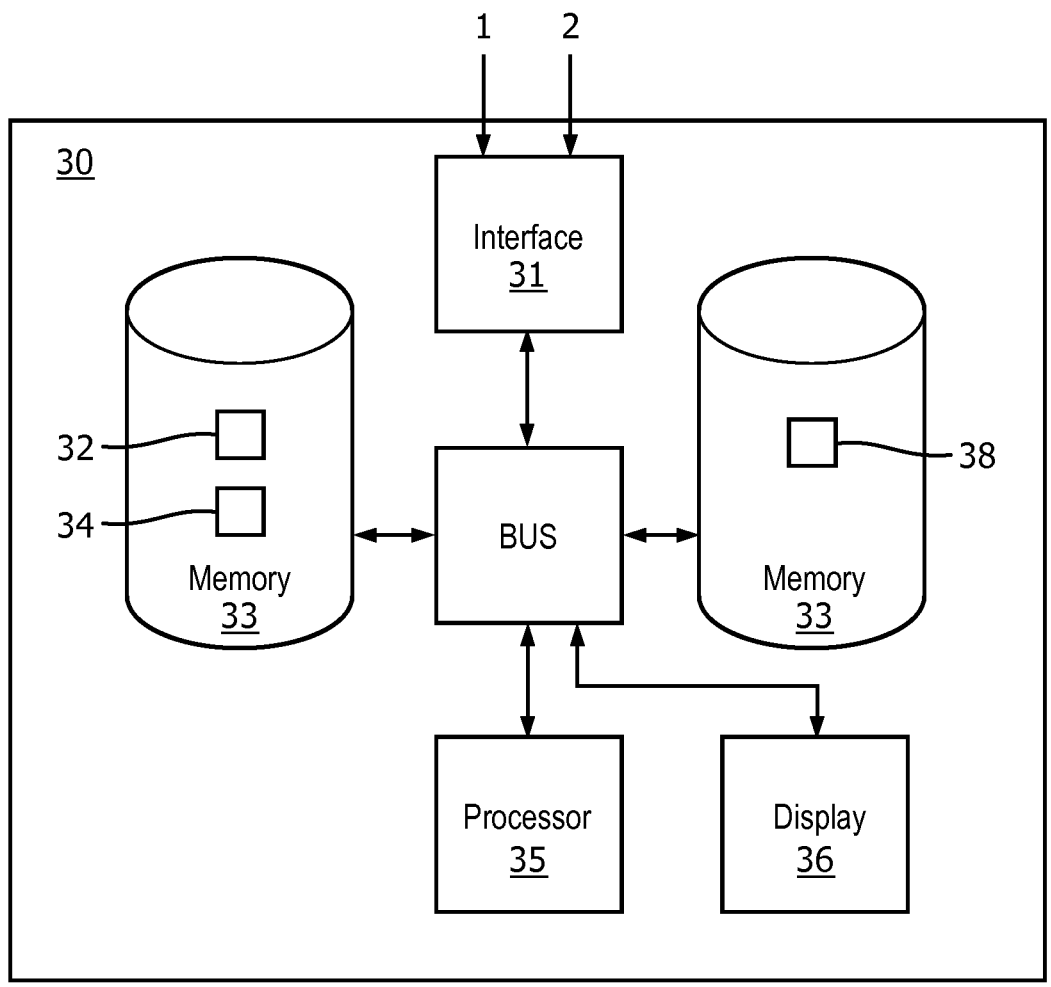
FIG. 2 is a block diagram of a workstation incorporating pose estimation and application units according to an embodiment of the present invention.

The ultrasound imaging probe 10 and the inertial tracking sensor 20 are operatively connected to a pose estimation unit 32. The pose estimation unit may be integral with a workstation 30, such as the Philips Invivo UroNav® system, where the pose estimation unit 32 is realized in software executed on a processor 35 in the workstation 30, as shown in FIG. 2. Alternatively, the pose estimation unit 32 may be realized in firmware, in a stand-alone processor executing integral software or a software program stored remotely or any other appropriate configuration as is known in the art. The operative connection of the ultrasound image probe 10 and the inertial tracking unit 20 with the pose estimation unit 32 is realized through interface 31, which may be a physical cable, such as an Ethernet cable suitable for transmitting sensor data and an associated connector. Alternatively, the interface 31 may be configured to transmit the ultrasound imaging data and the inertial sensor data wirelessly using RF, IR, or other wireless communication techniques.

The pose estimation unit 32 uses the image data stream 2 to estimate in-plane motion of a successive or final image frame from the image data stream relative to an initial image frame. The in-plane motion estimates are performed by registering the successive image frame to the initial image frame as is known in the art. The initial image frame and the registered successive image frame are then divided into a matrix of sub-planes, as is known in the art. Absolute out-of-plane distances are estimated for each sub-plane using speckle decorrelation, as is known in the art.

The pose estimation unit, in parallel with the in-plane motion estimates and out-of-plane distance estimates, estimates out-of-plane angles of rotation from the inertial sensor data.

Then, the pose estimation unit determines an out-of-plane translation between successive image frames by iteratively selecting planes with the estimated out-of-plane rotations by varying an out-of-plane offset. The out-of-plane offset is an estimation of the out-of-plane translation. Then, the pose estimation unit calculates the motion of each sub-plane for the estimated out-of-plane rotations and the selected plane, and computes the differences between the sub-plane absolute distances computed by speckle analysis and those calculated from the inertial data derived rotation and selected plane. Finally, the pose estimation unit minimizes for the root mean square of the differences for all selected planes.

According to an exemplary embodiment of the present invention, an application unit 34 uses the poses of the sequence of image frames to apply the image data in the imaging planes to perform an imaging procedure. For example, the poses can be used to fuse the imaging data with a 3D model of the imaging space for presentation on a display 36, as is known in the art. Alternatively, the poses can be used to provide the imaging data registered to features not visible on the ultrasound images on a display 36, as is known in the art.

According to an embodiment of the present invention, the pose estimation unit 32 receives image based tracking data 2 and inertial sensor data 1 and performs pose estimations for a sequence of image planes from the image based tracking data, where the image planes intersect and the axis of rotation of the final image plane around the initial image plane goes through the initial imaging plane.

Figure 3:
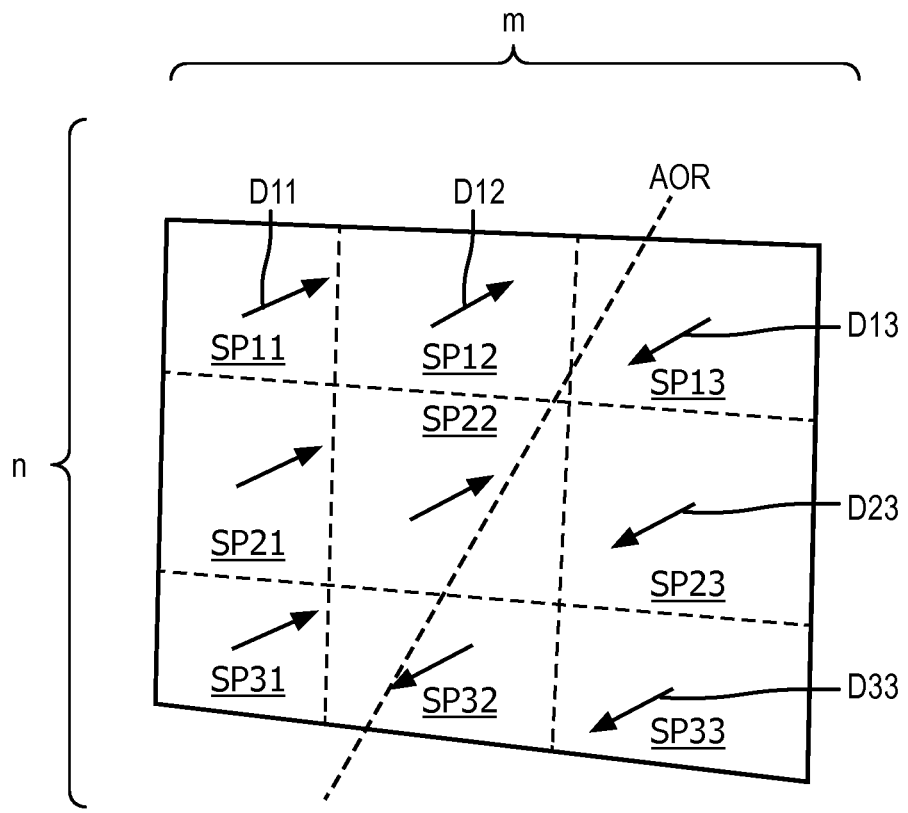
FIG. 3 is diagram showing out-of-plane rotation of an imaging plane sequence and creation of sub-planes according to an embodiment of the present invention.
Figure 4:
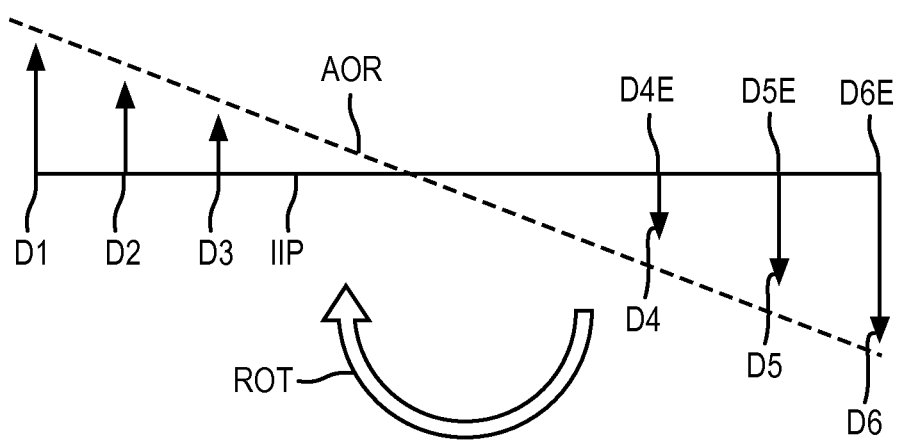
FIG. 4 is a diagram showing the difference between an actual out-of-plane rotation and estimated out-of-plane rotation using unenhanced speckle decorrelation.

Referring now to FIGS. 3 and 4, an initial image plane IIP from ultrasound imaging data is shown. The initial imaging plane can be divided into an (n×m) matrix of sub-planes, shown as sub-planes SP11-SP33 in FIG. 3. The out of plane motion around the axis of rotation AOR for the respective sub-planes is shown as distances D11-D33 where the distances to the left of the axis of rotation D11, D12, D21, D22, and D31 go into the paper (to the rear of the imaging plane) and the distances to the right of the axis of rotation come out of the paper (to the front of the imaging plane). When the imaging probe 10 is rotated around an axis going through the initial imaging plane, as shown in FIG. 3, the distances or displacements of sub-planes are in different directions. The distance estimates obtained for speckle decorrelation analysis, however are directionless. These kinds of rotations, where the axis of rotation goes through the initial imaging plane are clinically common and necessary, e.g. to change the view from "axial" to "sagittal". In this case, a method that relies on finding a single direction of out-of-plane motion for the entire image plane will not work, because part of the plane is moving on one direction and the other part of the plane is moving in the opposite direction.

Looking at the imaging plane IIP in one dimension in FIG. 4, the plane IIP is rotated by a rotation angle ROT around a pivot point on the initial image plane so that some distances D1 D3 are in the upward or positive direction and some distances D4-D6 are in the opposite, downward or negative direction. While the pivot point of rotation is shown on the plane in this simplified illustration, it will be understood by those skilled in the art that the axis of rotation will not typically lay on the initial imaging plane along its entire length. The speckle decomposition analysis, however assumes that all distances are positive, so the estimated distances for the positive motion D1-D3 will be the same as the actual distances, but the estimated distances for motion in the opposite direction D4E-D6E will not be the same as the actual distances.

To more accurately estimate a final pose in a pair of poses when the axis of rotation AOR goes through or intersects the initial imaging plane, an embodiment of the present invention uses data from an inertial sensor 20 rigidly attached to the ultrasound probe 10 to enhance the image based tracking, as follows.

An imaging region of interest (ROI) on the initial imaging plane IIP is divided into multiple sub-images or sub-planes SP11-SP33 to estimate out-of-plane motion at different locations of the image. Absolute distances are estimated for each sub-plane using speckle decorrelation. A plane of the estimated slope of the final plane is fitted to these individual estimations from the sub-planes SP11-SP33 which are iteratively assigned directionalities.

During this plane fit an axis of rotation AOR is introduced, where one side of the axis of rotation has opposite out-of-plane displacement direction with respect to the other side of the axis of rotation. The axis of rotation has known slope, but an unknown intersection point with the initial imaging plane. The RMS error calculated during this plane fit is minimized to obtain the best fit with an axis of rotation.

According to an embodiment of the present invention, the pose estimation unit 32 processes the imaging data stream 2 and the inertial sensor data stream 1, simultaneously. The image based tracking process buffers the last i image frames in memory 33, and process these image frames for in-plane and out of plane motion estimations. Preferably, i is less than 10, e.g. i=8. In-plane tracking is performed between the last I frames. Then log decompression and a speckle filter are applied to mask out the image regions from non-specular reflectors.

Each of the previous i–1 frames are aligned with respect to the i'th frame. That is, the frames are registered to each other. Two consecutive frames are registered to each other by optimization, where the objective is to minimize the difference between the reference frame (e.g. frame 1) and a transformed template frame (e.g. frame 2), subject to the transformation T, which can be rigid, affine, elastic, etc. . . . . The parameters of the transformation matrix can be solved iteratively using any non-linear solver. This registration provides the in-plane translations and the in-pane rotation of the successive image frame relative to the initial image frame.

Decorrelation calculations are performed between the i frame and the i-j frame pairs where (j=1, . . . (i−1)). The decorrelation calculations are performed on each sub-image of a (m×n) matrix of sub-images (i.e., sub-planes). The sub-images may be either overlapping or non-overlapping within each image plane.

Displacement (or out-of-plane distance) estimations are made based on previously obtained calibration scans which were acquired with known frame spacing. Calibration scans are performed by mounting the imaging probe on a positioner stage and moving at known increments, e.g. 0.1 mm. at each location a new image frame is acquired. The calibration images are also divided into multiple sub-images and decorrelation between them is calculated. For a set of N frames, N−1 1-lag decorrelations, N−2 2-lag decorrelations and so on . . . are calculated. All of the n-lag decorrelations are used to define a Gaussian calibration curve with respect to frame spacing.

Known plane fit optimization methods rely solely on image based tracking. As a result the plane fit optimizations are inaccurate. In embodiments of the present invention, an out-of-plane translation, with known angular pose from inertial tracking, is iteratively assumed. An axis of rotation is also iteratively assumed. Then displacements for sub-planes on one side of the axis of rotation (left side) are assumed to be positive, and displacements for sub-planes on the opposite side of the axis of rotation are assumed to be negative. The out-of-plane motion candidate with minimum RMS difference compared to the plane calculated based on speckle decorrelation analysis and iteratively assigned directionalities is picked.

Figure 5:
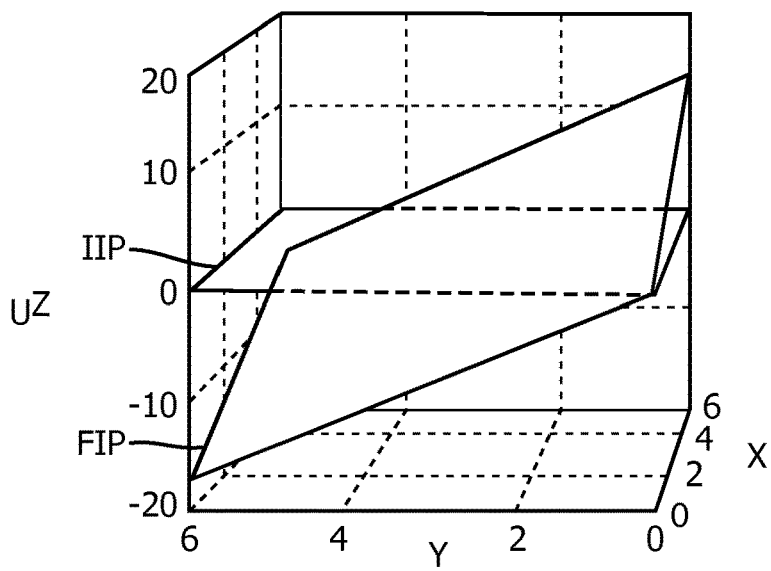
FIG. 5 is a diagram showing the actual initial and final pose of an image plane where the image planes intersect and the axis of rotation extends through the initial image plane.
Figure 6:
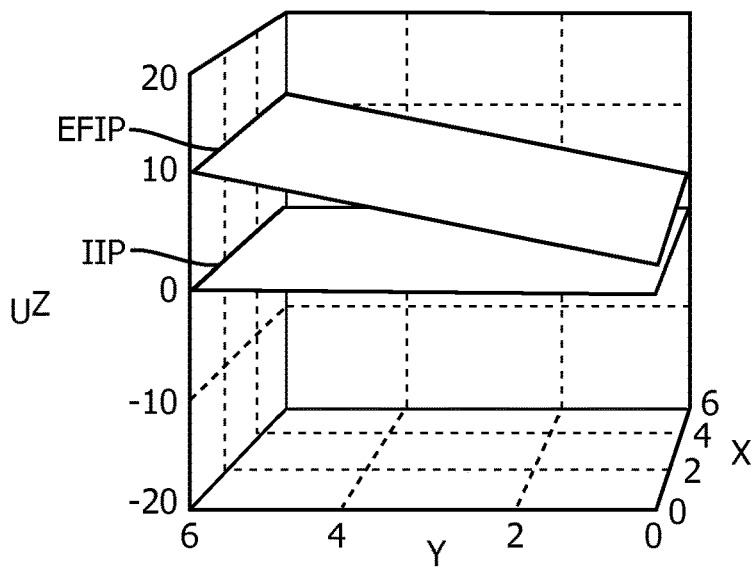
FIG. 6 is a diagram showing the actual initial pose of FIG. 5 and an estimated final pose of an image plane where the image planes intersect and the axis of rotation extends through the initial image plane, wherein the final pose is estimated using speckle decorrelation.
Figure 7:
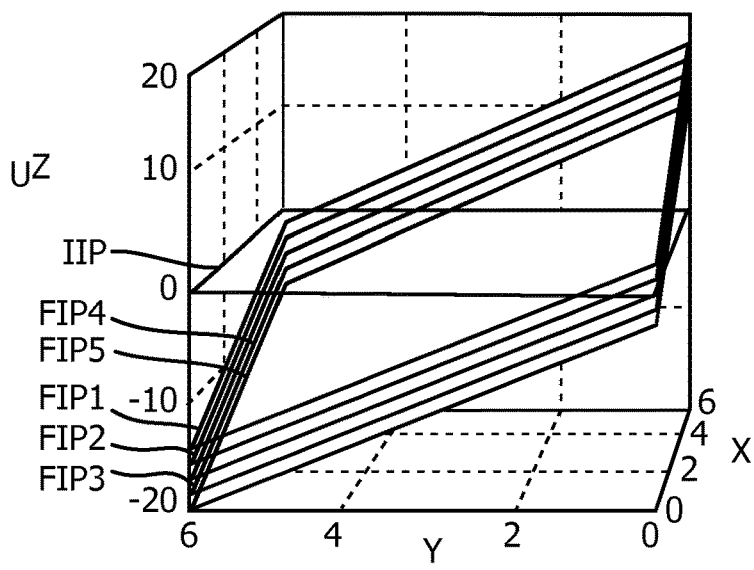
FIG. 7 is a diagram showing the initial pose of an image plane where the image planes intersect and the axis of rotation extends through the initial image plane, and a series of potential final poses with out-of-plane angles of rotation determined using inertial sensor data according to an embodiment of the present invention.

Referring to FIGS. 5 and 6, The initial imaging pose IIP and the final imaging pose intersect as shown in FIG. 5. The estimated final imaging pose EFIP based solely on image based tracking data as shown in FIG. 6 is inaccurate. If the final image plane (pose) is unknown, in an optimization method using solely image-based tracking, the optimization is a three degree of freedom problem (two out-of-plane rotations and an out-of-plane translation). This problem is computationally expensive and not very robust.

In an embodiment of the present invention, the slope of the final imaging plane FIP is known through inertial sensor data. In particular gyroscope measurements from an inertial sensor rigidly attached to the ultrasound probe can be used to calculate the orientation of the ultrasound probe and the imaging plane that is normal to the ultrasound probe. This reduces the optimization to a one degree of freedom problem—determining the out-of-plane translation (i.e., determining one of a series of parallel planes with the known angles of rotation).

The pose of the image plane is estimated by fitting a plane to the individual absolute out-of-plane displacements D11-D33 for each sub-plane. The slope (out-of-plane angles of rotation) of the final imaging plane FIP is known. The intercept of the axis of rotation and the initial imaging plane is a function of the out-of-plane translation, which is solved for iteratively. The final imaging plane FIP having the minimum RMS error defines the out-of-plane translation, and is used together with the image based in-plane translations and in-plane rotation and the inertial sensor based out-of-plane angles of rotation to define the final pose.

According to embodiments of the present invention, pose estimates from the pose estimation unit 32 are provided to an application unit 34. The application unit applies the pose estimates to provide images at a display 36 for use during an imaging procedure. For example, the application unit 34 may use the pose estimates to fuse the 2D image frames from the imaging data 2 to a 3D image volume, such as a pre-acquired x-ray scan or the like.

Alternatively these pose estimates can be used to reconstruct a 3D volumetric dataset of the region of interest, e.g. prostate, breast etc..... In a similar fashion to the current Uronav product created 3D prostate volumes using the pose information obtained through electromagnetic EM tracking.

Figure 8:
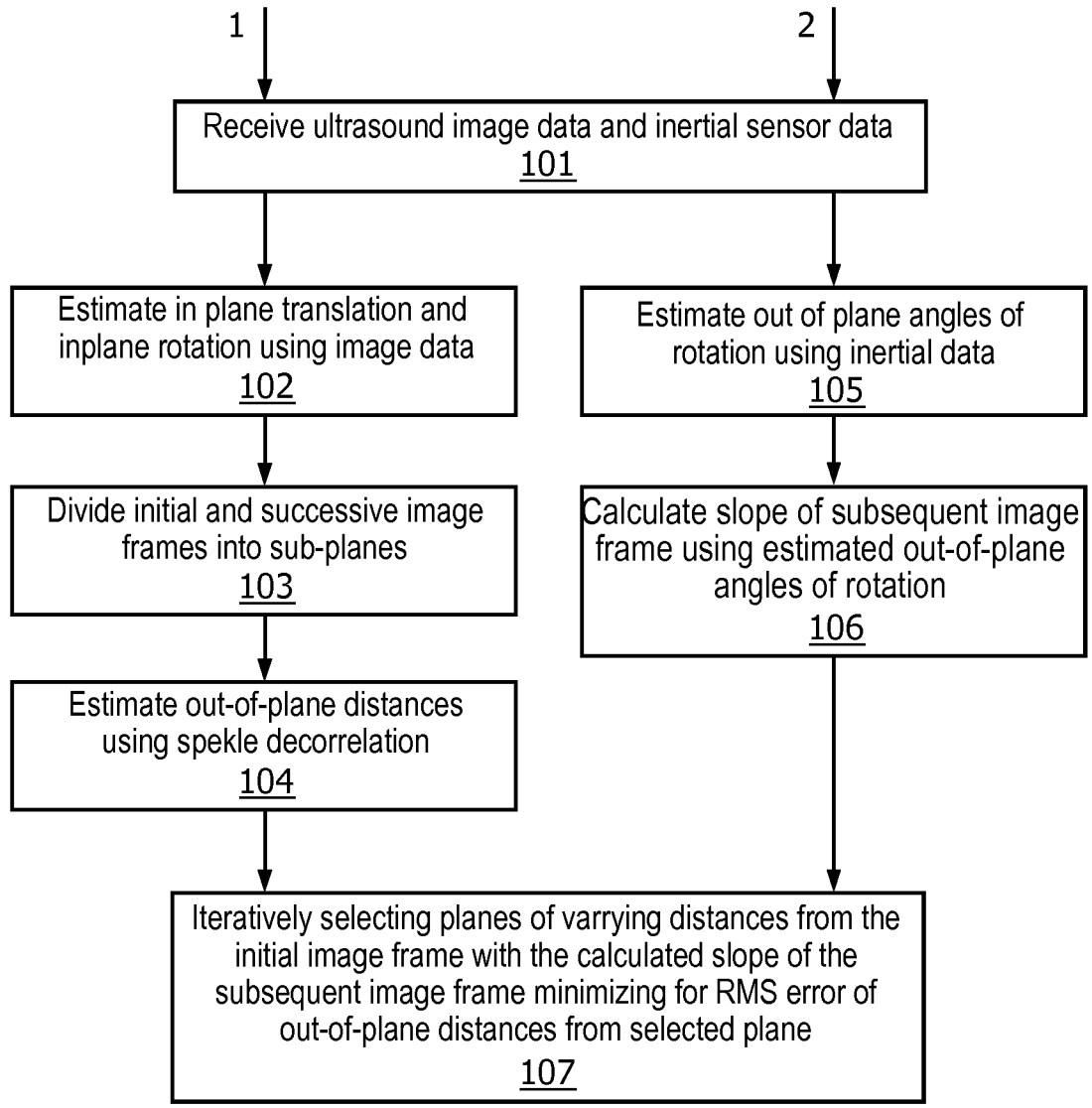
FIG. 8 is a flow diagram of a method of image based tracking using inertial data to optimize the final pose according to an embodiment of the present invention.

Referring now to FIG. 8, a method for tracking an ultrasound imaging probe according to an embodiment of the present invention is described. A pose estimation unit 32 receives an image data stream 2 comprising successive image planes from the ultrasound probe 10 an inertial data stream 1 from an inertial sensor unit 20 (Step 101).

In-plane translations and in-plane rotation are estimated by the pose estimation unit from the image data (Step 102). These in-plane motions are estimated using image registration, as is known in the art.

The pose estimation unit 32 divides an initial image frame of the image data stream and a successive or final image frame of the image data stream into a matrix of sub-images or sub-planes SP11-SP33 (Step 103). Then, the pose estimation unit 32 estimates absolute out-of-plane distances for each sub-plane using speckle decorrelation analysis of the image data stream, and estimates out-of-plane distances by iteratively assigning directionality to the absolute out of plane distances (Step 104).

Simultaneous with dividing the image plane in to subplanes and estimating out-of-plane distances, the pose estimation unit 32 estimates out-of-plane angles of rotation of the successive or final image frame from the inertial data stream (Step 105) and calculates a slope of the final plane from the axis of rotation (Step 106).

Figure 9:
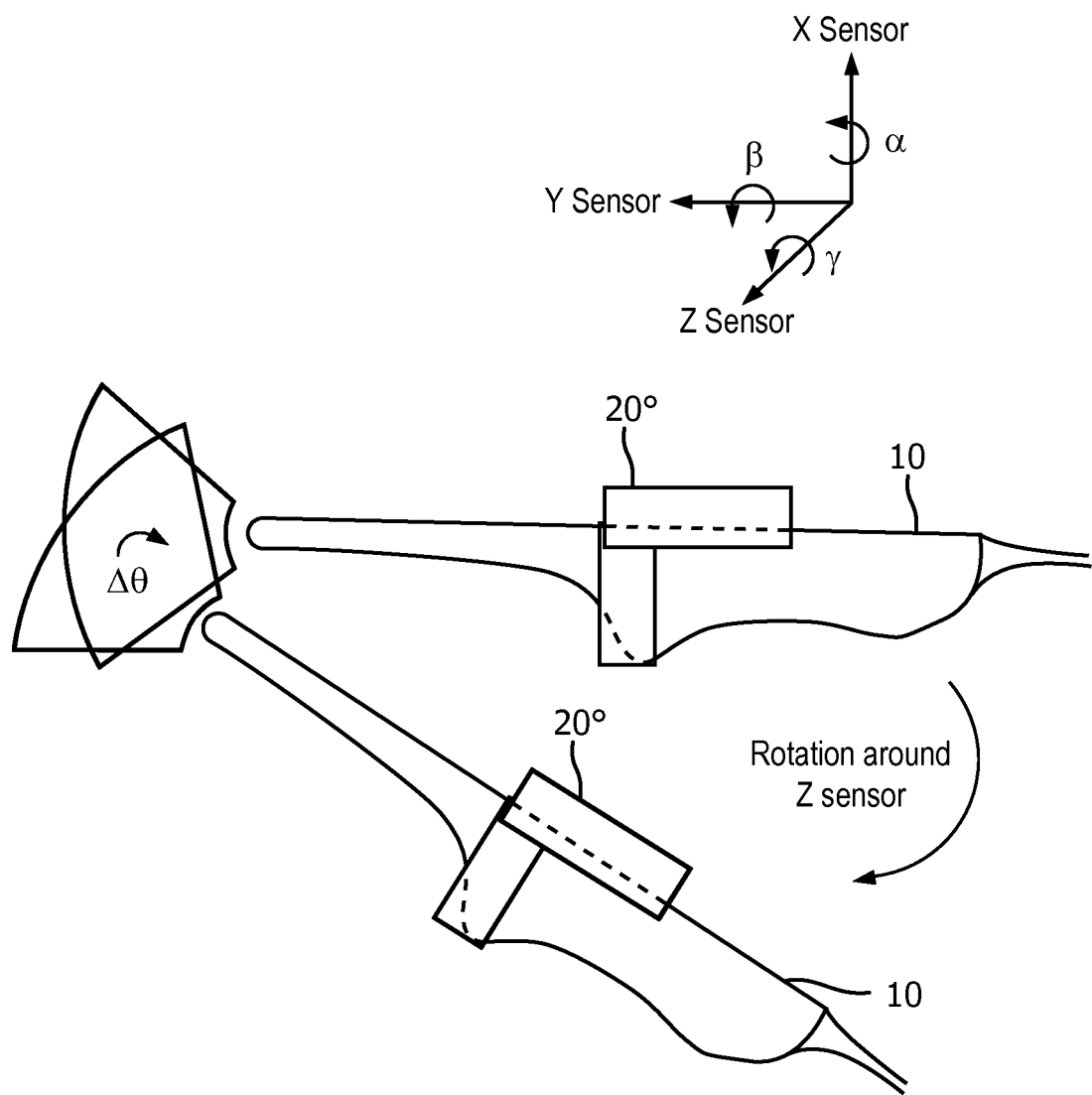
FIG. 9 is a diagram showing an ultrasound imaging probe rotating around the $Z_{sensor}$ axis and the associated in-plane image rotation according to an embodiment of the present invention.

The slope of the axis of rotation is defined with respect to the angles in FIG. 9. If probe is rotated only around the Y-sensor then the corresponding AOR is zero degrees. Rotation around the Z-sensor defines the slope of AOR (i.e. $\tan(\chi)$ where $\chi$ is the angle of rotation measured by the Z-sensor).

Then, the pose estimation unit 32 determines an out-of-plane translation between successive image frames by iteratively selecting planes with the estimated out-of-plane rotations by varying an out-of-plane offset. The out-of-plane offset is an estimation of the out-of-plane translation. Then, the pose estimation unit calculates the motion of each sub-plane for the estimated out-of-plane rotations and the selected plane, and computes the differences between the sub-plane absolute distances computed by speckle analysis and those calculated from the inertial data derived rotation and selected plane. Finally, the pose estimation unit minimizes for the root mean square of the differences for all selected planes.

This out-of-plane translation is combined with the in-plane translations and in-plane rotation estimated from the image data and the out-of-plane angles of rotation estimated from the inertial sensor data to provide a pose for the successive or final image frame relative to the initial image frame.

According to another embodiment of the present invention, an inertial sensor 20 is rigidly fixed to an ultrasound probe 10 and both the ultrasound probe and the sensor are operably attached to a pose estimation unit 32 to provide inertial data and imaging data, respectively, as shown in FIG. 1. In this embodiment the ultrasound probe is tracked using inertial data with an angle θ of in-plane rotation estimated using imaging data and substituted into the inertial data. The inertial sensor 20 can be fixed to the ultrasound probe 10 at any relative orientation with respect to the imaging plane. For the purposes of the following description, however, the case where the imaging axes $x_{image}$ and $y_{image}$ are parallel to the sensor axes $x_{sensor}$ and $y_{sensor}$ will be considered.

Both image data 2 and inertial sensor data 1 are sent to the pose estimation unit 32. The image data comprises a stream of successive image frames or 2D ultrasound image planes. The image frames are registered with respect to each other to calculate the in-plane translations and rotation.

Referring to FIG. 9 through 14, the image data 2 is received by the pose estimation unit as a stream of successive images or image frames. These image frames are registered with respect to each other to calculate the in-plane translations $\Delta x_{image}$ and $\Delta y_{image}$ and the in-plane rotation $\Delta\theta$ between frames k and k-1. Any registration method known in the art may be used to register the successive image frames. Also, any deformability assumption of the medium such as rigid, affine, or elastic may be used with the invention. Once the image rotation, $\Delta\theta$, between frames k and k-1 are obtained from the image data, the image rotation is used to replace the rotation around the z-axis of the sensor from the inertial sensor data. The rotation around the z-axis of the sensor is also the inertial rotation around the z-axis of the image for the assumed case of parallel axes.

Figure 10:
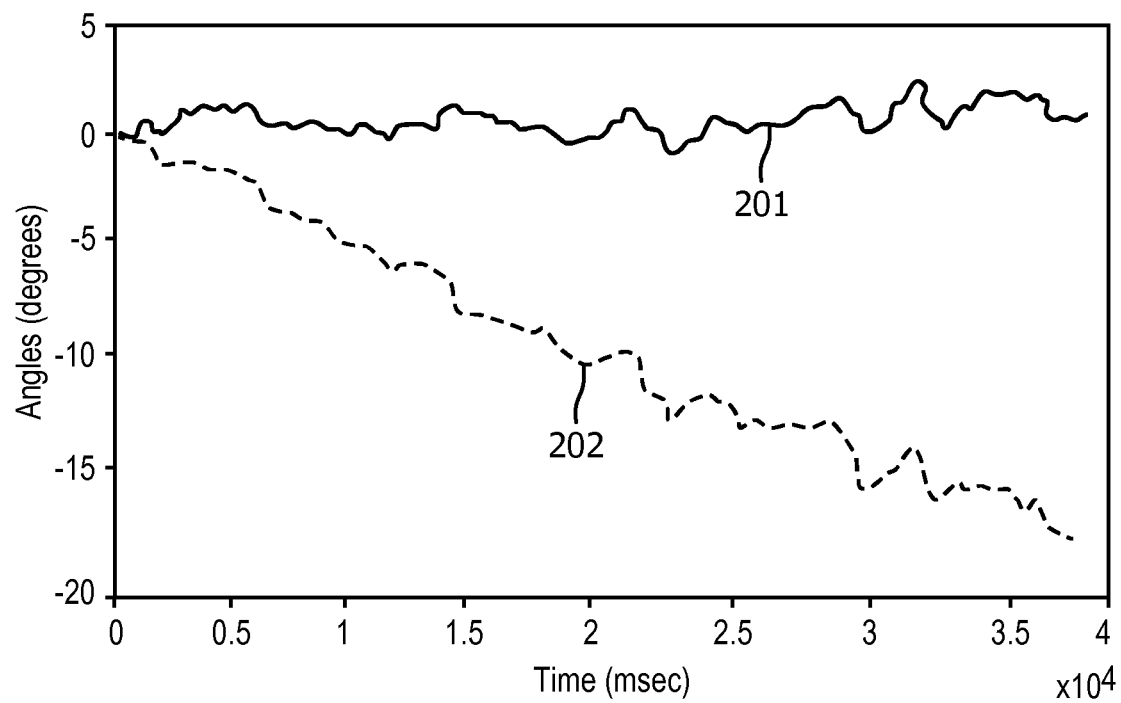
FIG. 10 is a plot of the in-plane angles of rotation of an image as determined by image based tracking and by inertial sensor tracking.

In this embodiment, the inertial sensor 20 comprises a gyroscope and accelerometer (IMU or MEMS). Typically, the inertial sensor has an acquisition rate of about 100 Hz, while image acquisition rates are about 20 Hz. The gyroscope data is buffered until the image data is available. Since the higher sampling rate of the inertial sensor improves performance of sensor fusion algorithms, instead of downsampling the existing gyroscope and accelerometer data to the image frame rate, rotation angle data obtained from ultrasound images are up-sampled to the inertial sensor sampling rate. Once the image based $\Delta\theta$ is calculated and available it is interpolated to estimate the corresponding $d\theta$ between inertial sensor sampling instances. The substitute angular rate is then computed as $\omega_{image}=d\theta/dt$. FIG. 10 shows angular positions 202 calculated from direct integration of gyroscope data 10 versus accumulation of image based calculations 201. The gyroscope bias is apparent after integration as the gyroscope curve 202 drifts away from the image based angles 201.

Figure 11:
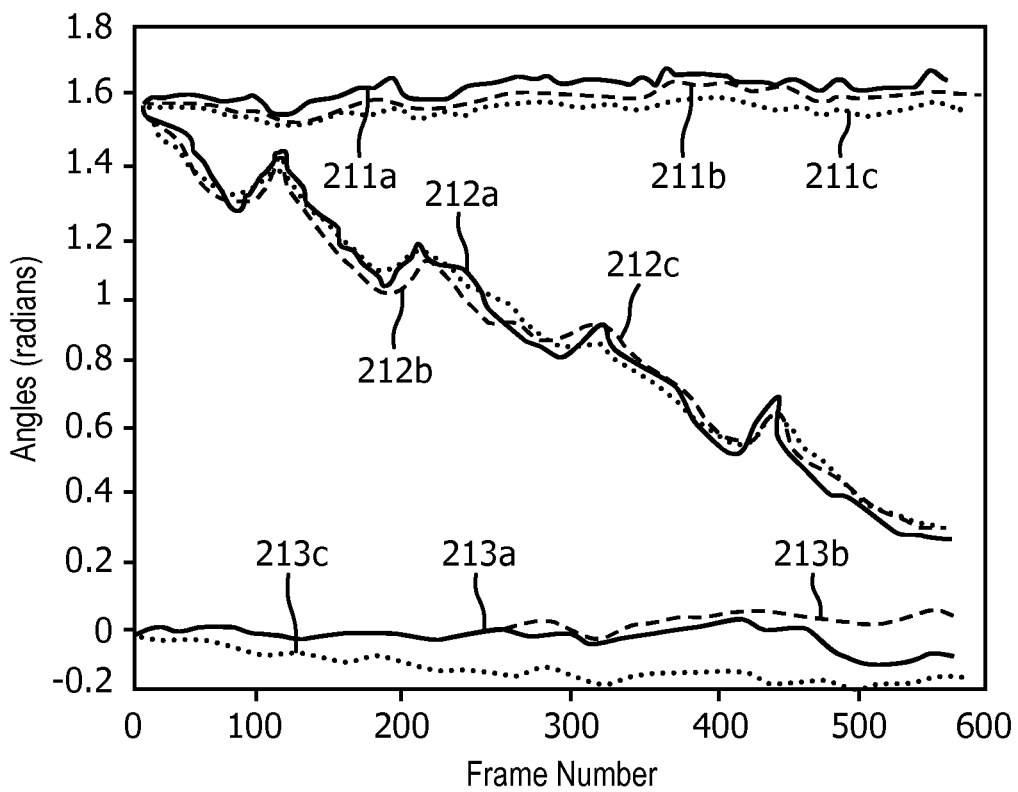
FIG. 11 is a plot showing three sets of three Euler angles, where for each Euler angle, curves are provided representing: (1) tracking using inertial sensors to estimate three rotations; (2) tracking using inertial and image based tracking by substituting the gyroscope z-axis measurements with image based in-plane rotation according to an embodiment of the present invention, and (3) ground truth EM tracking.

The substitute angles θ (the in-plane rotation calculated from image data) are then used in fusion algorithm to estimate the image plane pose. Results of the fusion algorithm are shown in FIG. 11. The curve using image information to partially substitute for gyroscope data (the present embodiment shown as a solid lines) 211a, 212a, 213a is shown with the curve using gyroscope data only (dotted lines) 211c, 212c, 213c and ground truth curves from electromagnetic tracking (dashed lines) 211b, 212b, 213b. As demonstrated in FIG. 11, when in-plane angles from ultrasound imaging data are used in place of one axis of rotation from gyroscope data, the Euler angles track closer to the ground truth EM based Euler angles.

Figure 12:
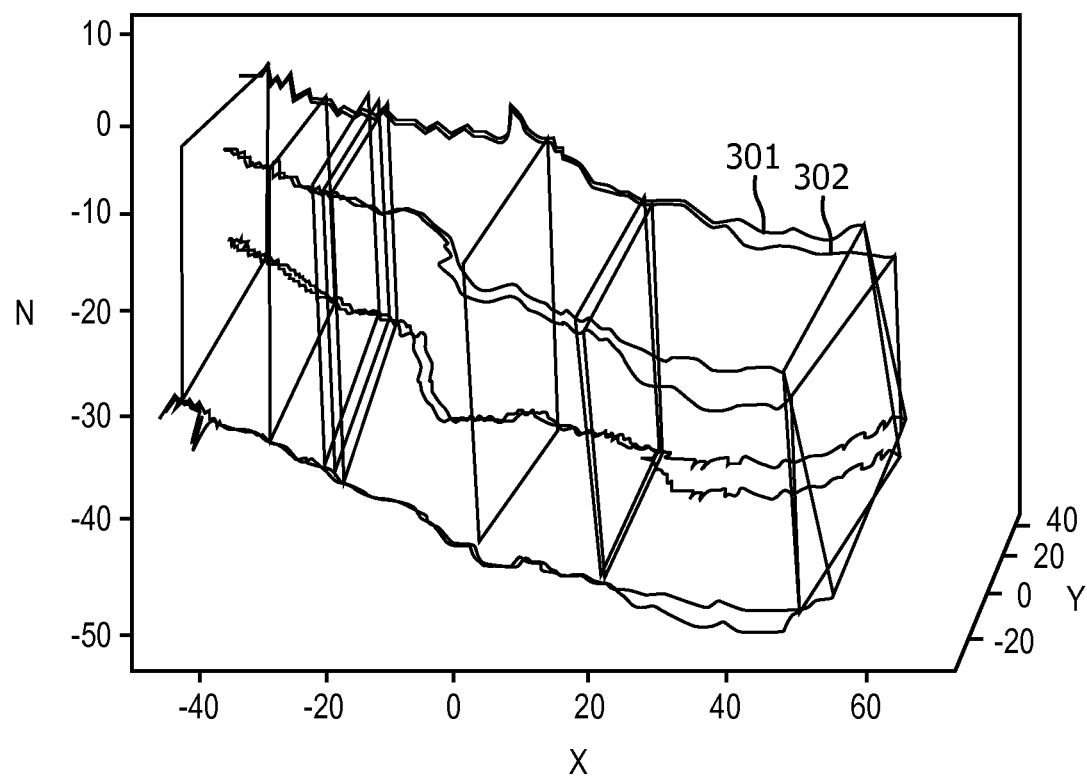
FIG. 12 is an image of wireframe reconstructions of ultrasound image locations using inertial tracking compared EM tracking.
Figure 13:
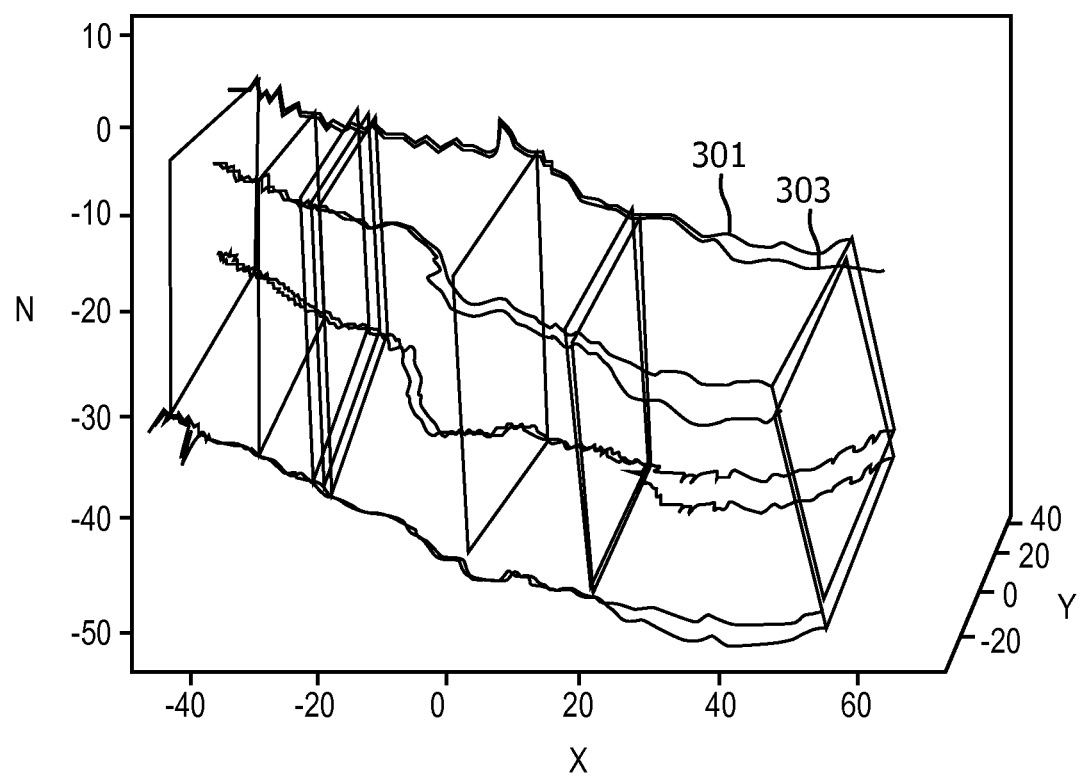
FIG. 13 is an image of wireframe reconstructions using inertial tracking for two axes and image based tracking of in-plane rotation according to an embodiment of the present invention compared to EM tracking.
Figure 14:
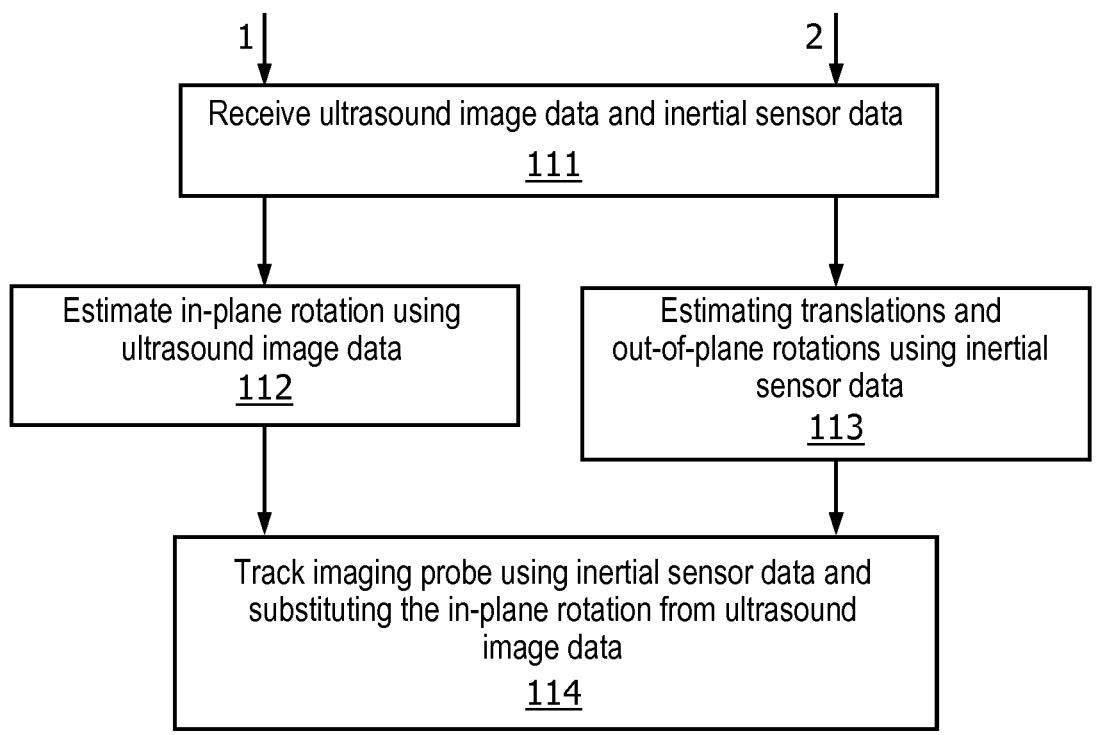
FIG. 14 is a flow diagram of a method of tracking using inertial sensors in which an image based in-plane angle of rotation is replacing the measurements from one of the gyroscope axes.

In this embodiment, the pose estimations using image based estimates for in-plane angles of rotation are provided to an application unit 36. The application unit performs wireframe 3D volumetric reconstruction using the image frames and estimated poses, then displays the wireframe reconstruction on display 36. The poses using image based estimates of the in-plane rotation give a better RMS error compared to the ground truth EM tracked frames. RMS error using only inertial sensor data to estimate poses is 2.96 mm. The present embodiment substituting in-plane angles of rotation estimated from imaging data decreases the RMS error to 2.76 mm. As shown in FIGS. 12 and 13, the reconstruction 302 using poses estimated from only inertial sensor data has an angular mismatch from the EM ground truth 301 (FIG. 12), while the reconstruction 303 using poses where in-plane rotation was estimated using ultrasound imaging data has less mismatch from the EM ground truth 301 (FIG. 13).

The invention may take the form of a computer program product accessible from a computer-usable or computer-readable medium providing program code for use by or in connection with a computer or any instruction execution system or device. For the purposes of this description, a computer-usable or computer readable medium may be any apparatus that can contain, store, communicate, propagate, or transport the program for use by or in connection with the instruction execution system, apparatus, or device.

The foregoing method may be realized by a program product comprising a machine—readable media having a machine-executable program of instructions, which when executed by a machine, such as a computer, performs the steps of the method. This program product may be stored on any of a variety of known machine-readable media, including but not limited to compact discs, floppy discs, USB memory devices, and the like.

The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk an optical disk. Current examples of optical disks include compact disk-read only memory (CD-ROM), compact disk-read/write (CD-R/W) and DVD.

The preceding description and accompanying drawing are intended to be illustrative and not limiting of the invention. The scope of the invention is intended to encompass equivalent variations and configurations to the full extent of the following claims.

What is claimed is:

1. An ultrasound imaging system with enhanced ultrasound imaging probe tracking comprising:
    an ultrasound imaging probe providing an image data stream of sequential image frames on image planes;
    an inertial tracking sensor rigidly fixed to the ultrasound probe and providing an inertial data stream;
    a real-time pose estimation unit receiving and processing the image data stream and the inertial data stream to estimate an ultrasound probe pose for a successive image frame of the sequential image frames by:
        estimating in-plane translations and rotation between an initial image frame and the successive image frame from the image data stream by registering the successive image frame to the initial frame;
        dividing a region of interest in the initial image frame and the registered successive image frame into a matrix of sub-planes;
        estimating out of plane distances for each sub-plane using speckle decorrelation analysis;
        estimating an estimated out of plane rotation between the initial image frame and the successive image frame from the inertial data stream; and
        determining an out-of-plane translation between the initial image frame and the successive image frame by:
            a) iteratively selecting a plurality of different out-of-plane translational offsets, each having the estimated out-of-plane rotation, from an initial imaging plane;
            b) calculating a translational displacement from the initial imaging plane to each sub-plane for each of the plurality of translational offsets;
            c) computing differences between the sub-plane distances computed by speckle analysis and the calculated translational displacements for each of the plurality of translational offsets; and
            d) selecting one of the out-of-plane translational offsets having a minimum root mean square of the differences as the out-of-plane translation.

2. The ultrasound imaging system of claim 1, wherein the inertial tracking sensor is an inertial measurement unit (IMU) comprising three mutually perpendicular linear acceleration sensors and three mutually perpendicular gyroscope sensors and the inertial data stream comprises linear acceleration data from the acceleration sensors and orientation data from the gyroscope sensors or a combination of both.

3. The ultrasound imaging system of claim 1, wherein the pose estimation unit is realized in a workstation.

4. The ultrasound imaging system of claim 3, wherein the workstation further comprising an application unit applying the estimated ultrasound probe pose to fuse the image data for the pose with an image volume to generate a fused image and display the fused image on a display.

5. A method for tracking an ultrasound imaging probe, comprising the steps of:
    receiving an image data stream comprising sequential image frames from the ultrasound probe and an inertial data stream from an inertial sensor unit rigidly attached to the ultrasound imaging probe;
    estimating in-plane translations and rotation between an initial image frame and a successive image frame of the sequential image frames by registering the successive image frame to the initial image frame;
    dividing a region of interest in the initial image frame and the registered successive image frame of the image data stream into a matrix of sub-planes;
    estimating out of plane distances for each sub-plane using speckle decorrelation analysis;
    estimating an out-of-plane rotation between the initial image frame and the successive image frame from the inertial data stream; and
    determining an out-of-plane translation between the initial image frame and the successive image frame by:
        a) iteratively selecting a plurality of different out-of-plane translational offsets, each having the estimated out-of-plane rotation, from an initial imaging plane;
        b) calculating a translational displacement from the initial imaging plane to each sub-plane for each of the plurality of translational offsets;
        c) computing differences between the sub-plane distances computed by speckle analysis and the calculated translational displacements for each of the plurality of translational offsets; and
        d) selecting one of the out-of-plane translational offsets having a minimum root mean square of the differences as the out-of-plane translation.

6. The method of claim 5, further comprising the steps of:
    assigning the translational offset with the minimum root mean square of the differences as the final pose estimate; and
    applying the final pose estimate to fuse successive images for display during an imaging procedure.

* * * * *